US00PP20963P2

(12) United States Plant Patent
Bartels

(10) Patent No.: US PP20,963 P2
(45) Date of Patent: Apr. 27, 2010

(54) ROSE PLANT NAMED 'EMPINTOIMP'

(50) Latin Name: *Rosa hybrida*
Varietal Denomination: Empintoimp

(75) Inventor: Gosen B. H. Bartels, Aalsmeer (NL)

(73) Assignee: Bartels Rose Breeding B.V., Aalsmeer (NL)

( * ) Notice: Subject to any disclaimer, the term of this patent is extended or adjusted under 35 U.S.C. 154(b) by 0 days.

(21) Appl. No.: 12/315,312

(22) Filed: Dec. 2, 2008

(51) Int. Cl.
*A01H 5/00* (2006.01)

(52) U.S. Cl. ..... Plt./139

(58) Field of Classification Search ..... Plt./108, Plt./139, 140

See application file for complete search history.

*Primary Examiner*—June Hwu
(74) *Attorney, Agent, or Firm*—C. A. Whealy

(57) ABSTRACT

A new and distinct cultivar of Rose plant named 'Empintoimp', characterized by its long and upright flowering stems; strong plants; dark red-colored flowers; and excellent post-production longevity.

1 Drawing Sheet

Botanical designation: *Rosa hybrida.*
Cultivar denomination: 'Empintoimp'.

BACKGROUND OF THE INVENTION

The present Invention relates to a new and distinct cultivar of Rose plant, botanically known as *Rosa hybrida*, commercially used as a cut flower Rose, and hereinafter referred to by the name 'Empintoimp'.

The new Rose plant is a product of a planned breeding program conducted by the Inventor in Aalsmeer, The Netherlands. The objective of the breeding program was to develop new freely-flowering cut flower Rose varieties with attractive flower colors and excellent postproduction longevity.

The new Rose plant is a naturally-occurring whole plant mutation of *Rosa hybrida* 'Empinto', not patented. The new Rose was discovered and selected by the Inventor as a single flowering plant from within a population of plants of 'Empinto' in a controlled greenhouse environment in Aalsmeer, The Netherlands in 2008.

Asexual reproduction of the new Rose by cuttings at Aalsmeer, The Netherlands, has shown that the unique features of this new Rose plant are stable and reproduced true to type in successive generations of asexual reproduction.

SUMMARY OF THE INVENTION

The following traits have been repeatedly observed and are determined to be the unique characteristics of 'Empintoimp'. These characteristics in combination distinguish 'Empintoimp' as a new and distinct Rose cultivar:

1. Long and upright flowering stems.
2. Glossy dark green-colored leaves.
3. Dark red yellow-colored flowers.
4. Excellent postproduction longevity.
5. Resistant to Powdery Mildew.

Plants of the new Rose differ from plants of the parent, 'Empinto', primarily in flower bud size as plant of the new Rose have taller flowers buds than plants of 'Empinto'.

Plants of the new Rose can be compared to plants of *Rosa hybrida* 'Freedom', not patented. In side-by-side comparisons conducted in Aalsmeer, The Netherlands, plants of the new Rose differed from plants of 'Freedom' in the following characteristics:

1. Plants of the new Rose had glossier leaves than plants of 'Freedom'.
2. Outer flower petals of plants of the new Rose did not bronze or blacken whereas outer flower petals of plants of 'Freedom' bronzed and blackened.
3. Plants of the new Rose were resistant to Downy and Powdery Mildew whereas plants of 'Freedom' were not resistant to Downy and Powdery Mildew.

BRIEF DESCRIPTION OF THE PHOTOGRAPH

The accompanying colored photograph illustrates the overall appearance of the new Rose plant, showing the colors as true as it is reasonably possible to obtain in colored reproductions of this type. Colors in the photograph may differ slightly from the color values cited in the detailed botanical description which accurately describe the colors of the new Rose.

The photograph comprises a side perspective view of typical flowering stems of 'Empintoimp'.

DETAILED BOTANICAL DESCRIPTION

Plants of the new Rose have not been observed under all possible environmental conditions. The phenotype may vary somewhat with variations in environment such as temperature and light intensity, without, however, any variance in genotype. The aforementioned photographs, following observations and measurements describe plants grown during the summer and early autumn in Aalsmeer, The Netherlands, in a glass-covered greenhouse and under commercial production practices. Plants had been growing for ten months when the photographs and description were taken. During the production of the plants, day temperatures averaged 20° C., night temperatures averaged 18° C. and light levels averaged 10 kilolux. In the following description, color references are made to The Royal Horticultural Society Colour Chart, 2001 Edition, except where general terms of ordinary dictionary significance are used.

Botanical classification: *Rosa hybrida* 'Empintoimp'.

Parentage: Naturally-occurring whole plant mutation of *Rosa hybrida* 'Empinto', not patented.

Propagation:

*Type.*—By cuttings.

*Time to initiate roots.*—About twelve days at 20° C.

*Time to produce a rooted young plant.*—About five weeks at 20° C.

*Root description.*—Fleshy, medium in thickness; white in color.

*Rooting habit.*—Moderately branching; moderately dense.

Plant description:

*Plant form.*—Upright plant habit; long and upright flowering stems.

*Growth habit.*—Vigorous; freely basal branching habit; dense and bushy growth habit; about 25 flowering stems develop per year.

*Plant height.*—About 70 cm to 80 cm.

*Plant width (spread).*—About 30 to 40 cm.

*Lateral branches (peduncles).*—Length: About 70 cm to 80 cm. Diameter: About 5 mm. Internode length: About 7 cm. Strength: Strong. Texture: Pubescent. Color: Close to 137B. Thorns: Shape: Triangular with sharp acuminate apices. Height: About 1 cm. Diameter, at base: About 6 mm. Color, immature and mature: Close to 173A.

Foliage description:

*Arrangement.*—Alternate; compound with typically five to seven leaflets per leaf.

*Terminal leaflet length.*—About 8 cm.

*Terminal leaflet width.*—About 5 cm.

*Lateral leaflet length.*—About 7 cm.

*Lateral leaflet width.*—About 4 cm.

*Leaflet shape.*—Narrowly ovate.

*Leaflet apex.*—Acuminate.

*Leaflet base.*—Obtuse.

*Leaflet margin.*—Serrate.

*Leaflet texture, upper and lower surfaces.*—Smooth, glabrous.

*Leaflet venation pattern.*—Pinnate.

*Leaflet color.*—Developing leaflets, upper surface: Close to 137A tinged with close to 60A. Developing leaflets, lower surface: Close to 137B. Fully expanded leaflets, upper surface: Close to 139A; venation, close to 139B. Fully expanded leaflets, lower surface: Close to 137B; venation, close to 137B.

*Petioles, leaves.*—Length: About 3.5 cm. Diameter: About 3 mm. Texture, upper and lower surfaces: Smooth, glabrous. Color, upper and lower surfaces: Close to 139B.

*Petioles, leaflets.*—Length: About 3 mm. Diameter: About 2 mm. Texture, upper and lower surfaces: Smooth, glabrous. Color, upper and lower surfaces: Close to 139B.

*Stipules.*—Quantity/arrangement/appearance: Two, adnate to the petiole, leafy. Length: About 2 cm. Width: About 1 mm to 2 mm. Shape: Lanceolate. Apex: Acuminate. Base: Truncate. Margin: Serrate. Texture, upper and lower surfaces: Smooth, glabrous. Venation pattern: Pinnate. Color, upper and lower surfaces: Close to 139B.

Flower description:

*Flower type and habit.*—Consistently symmetrical rosette flowers; one flower per terminal.

*Flowering season.*—Year-round under greenhouse conditions, optimal flowering from spring through autumn under garden conditions; flowering intermittent.

*Flower diameter.*—About 10 cm.

*Flower depth (height).*—About 4.5 cm.

*Flower longevity on plant.*—About 14 days; flowers persistent.

*Flower longevity as a cut flower.*—About 12 days.

*Fragrance.*—None detected.

*Flower buds.*—Shape: Ovoid. Length: About 4 cm. Diameter: About 3 cm to 4 cm. Color: Close to 53A.

*Petals.*—Quantity: Numerous; about 35 per flower. Length: About 6 cm. Width: About 4.5 cm. Shape: Broadly elliptical. Apex: Acute. Base: Obtuse. Margin: Entire. Texture, upper and lower surfaces: Smooth, glabrous; velvety. Color: When opening, upper and lower surfaces: Close to 53A. Fully opened, upper and lower surfaces: Close to 53A; color does not fade with development.

*Sepals.*—Quantity per flower: Typically five. Length: About 4.5 cm. Width: About 1.2 cm. Shape: Lanceolate. Apex: Acuminate. Base: Obtuse. Margin: Entire. Texture, upper and lower surfaces: Smooth, glabrous. Color: When opening and fully opened, upper surface: Close to 139A. When opening and fully opened, lower surface: Close to 139A.

*Reproductive organs.*—Stamens: Quantity: About 90 per flower. Anther length: About 3 mm. Anther shape: Elliptical. Anther color: Close to 7A. Pollen amount: Scarce. Pollen color: Close to 155D. Pistils: Quantity: About 70 per flower. Pistil length: About 1.2 cm. Stigma color: Close to 155D. Style length: About 8 mm. Style color: Close to 155D.

*Seeds/fruits.*—Seed and fruit development has not been observed on plants of the new Rose.

Pathogen/pest resistance: Plants the new Rose have been observed to be resistant to Downy and Powdery Mildew. Plants of the new Rose have not been observed to be resist to pests and other pathogens common to Roses.

Temperature tolerance: Plants of the new Rose have been observed to tolerate temperatures ranging from 1° C. to 35° C.

It is claimed:

1. A new and distinct Rose plant named 'Empintoimp' as illustrated and described.

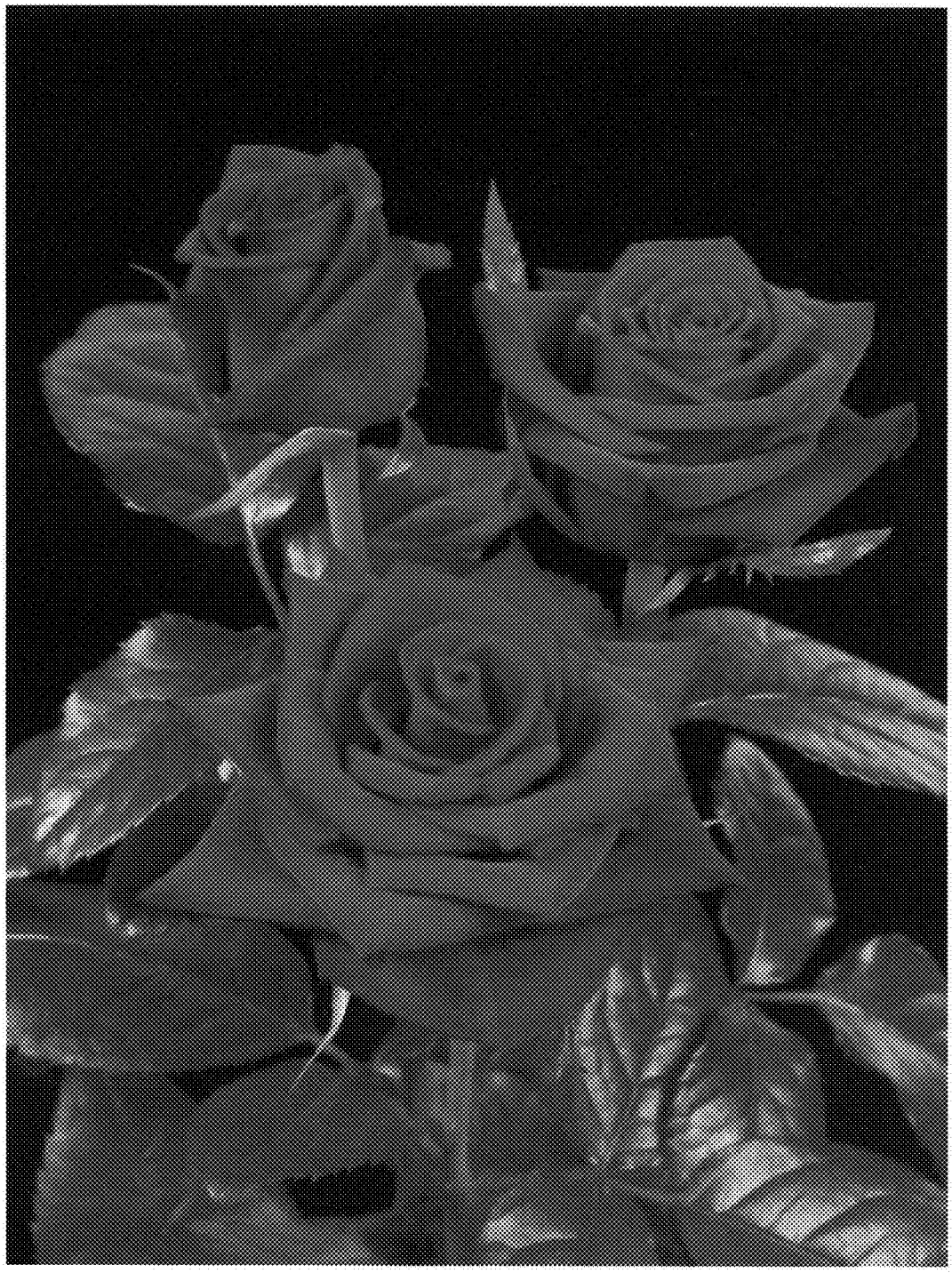

* * * * *